US006020522A

United States Patent [19]

Ishii et al.

[11] Patent Number: 6,020,522

[45] Date of Patent: Feb. 1, 2000

[54] PROCESS FOR PRODUCING AROMATIC HYDROXYCARBOXYLIC ACID DERIVATIVES

[75] Inventors: Yasutaka Ishii, Takatsuki; Tatsuya Nakano, Himeji, both of Japan

[73] Assignee: Daicel Chemical Industries, Ltd., Osaka, Japan

[21] Appl. No.: 09/075,250

[22] Filed: May 11, 1998

[30] Foreign Application Priority Data

May 20, 1997 [JP] Japan .................................... 9-129471

[51] Int. Cl.$^7$ ...................................................... C07C 51/16

[52] U.S. Cl. ............................ 562/410; 562/412; 560/64; 560/66

[58] Field of Search .................................... 562/412, 410; 560/64, 66

[56] References Cited

FOREIGN PATENT DOCUMENTS 8 24962A1 2/1998 European Pat. Off. .

8-038909A 2/1996 Japan .

OTHER PUBLICATIONS

Journal of Organic Chemistry—vol. 61, No. 14, 1996, 4520–4526—Y. Ishii et al.—"Alkane Oxidation with Molecular Oxygen Using a New Efficient Catalytic System: N–Hydroxyphthalimide (NHPI) Combined with Co(acac)$_n$ (N=2 or 3)+".

Journal of Organic Chemistry—vol. 60, No. 13, 1995, 3934–3935, Y. Ishii et al.—"A Novel Catalysis of N–Hydroxyphthalimide in the Oxidation of Organic Substrates by Molecular Oxygen".

Chem Abst CN 126: 237962 (1997).

*Primary Examiner*—Paul J. Killos

*Attorney, Agent, or Firm*—Birch, Stewart, Kolasch & Birch, LLP

[57] ABSTRACT

A methyl group-containing aromatic compound having a phenolic hydroxyl group protected by a protecting group, is oxidized with oxygen to provide an aromatic hydroxycarboxylic acid derivative. The protecting group includes, for example, an acyl group.

12 Claims, No Drawings

PROCESS FOR PRODUCING AROMATIC HYDROXYCARBOXYLIC ACID DERIVATIVES

FIELD OF THE INVENTION

This invention relates to a process for producing an hydroxybenzoic acid derivative and other aromatic hydroxycarboxylic acid derivatives.

BACKGROUND OF THE INVENTION

Among hydroxybenzoic acids, o-hydroxybenzoic acid (e.g., salicylic acid) is used as a dye or an intermediate thereof, an antiseptic agent, a stock agent, a keratin solubilizor, a dermatitis therapy and so forth. In particular, an acetylsalicylic acid (aspirin), a derivative of salicylic acid, is a very important compound as an antipyrin, an analgesic and a resolution agent. P-hydroxybenzoic acid is employed as a raw material of polyesters and an ester derivative thereof is used as an antibacteria agent or a stock agent.

O-hydroxybenzoic acid or p-hydroxybenzoic acid is usually produced by Kolbe-Schmit reaction using phenol and sodium hydroxide or potassium hydroxide via sodium hydroxybenzoate or potassium hydroxybenzoate. Since the hydroxybenzoate is industrially converted to an hydroxybenzoic acid having a free hydroxyl group by an acid such as sulfuric acid, a treatment of metal salts (e.g., sodium sulfonate, potassium sulfonate) produced as by-products is required.

Japanese Patent Application Laid-open No. 38909/1996 (JP-A-8-38909) provides an oxidation process using an imide compound (e.g., N-hydroxyphthalimide) as a catalyst at a stage of oxidation of a substrate (e.g., hydrocarbon) with oxygen. When this oxidation process is applied to an aromatic compound having a methyl group, aromatic compounds having a carboxyl group may be formed. However, when a compound such as cresol is used, it is difficult to obtain an hydroxybenzoic acid.

SUMMARY OF THE INVENTION

It is, therefore, an object of the present invention to provide a process for producing an aromatic hydroxycarboxylic acid derivative from an aromatic compound having a hydroxyl group and a methyl group.

It is another object of the present invention to provide a process for producing an aromatic hydroxycarboxylic acid derivative without producing a metal salt as by products.

The inventors of the present invention did intensive investigation to accomplish the above objects, and as a result, found that after protecting a phenolic hydroxyl group with a protecting group, cresol could be subjected to an oxidation reaction with oxygen in the presence of an imide compound to produce an aromatic hydroxycarboxylic acid derivative.

A process for producing an aromatic hydroxycarboxylic acid derivative of the preset invention comprises contacting a methyl group-containing aromatic compound with oxygen in the presence of an imide compound, wherein a phenolic hydoroxyl group of the aromatic compound is protected by a protecting group (hereinafter referred to simply as "an aromatic compound protected by a protecting group" or "a protecting group-introduced aromatic compound"), wherein the imide compound shown by the following formula (1);

(1)

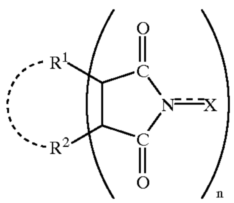

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may bond together to form a double bond or an aromatic and non-aromatic ring; X represents an oxygen atom or a hydroxyl group; and n denotes an integer of 1 to 3.

Examples of the protecting group include $C_{2-6}$ aliphatic acyl groups. Incidentally, the protecting group may be eliminated from an aromatic hydroxycarboxylic acid formed by contacting with oxygen and protected by a protecting group. In an aromatic hydroxycarboxylic acid formed by contacting with oxygen and protected by an acyl group, for example, the acyl group may be eliminated by a reaction with an alcohol.

Incidentally, in the specification "an aromatic compound having a phenolic hydroxyl group and a methyl group simply referred to as "an aromatic compound".

DETAILED DESCRIPTION OF THE INVENTION (An aromatic compound)

In an aromatic compound, an aromatic ring is substituted with at least one phenolic hydroxyl group and at least one methyl group. An aromatic compound includes, for example, o-cresol, m-cresol, p-cresol, methylnaphthols such as 6-methyl-α-naphthol and 6-methyl-β-naphthol, an aromatic compound having plural methyl groups (e.g., 2,3-xylenol, 2,4-xylenol, 2,5-xylenol, 2,6-xylenol, 3,4-xylenol, 3,5-xylenol, dimethyl-α-naphthol and dimethyl-β-naphthol), an aromatic compound having plural hydroxyl groups (e.g., 2,3-dihydroxytoluene, 2,4-dihydroxytoluene, 2,5-dihydroxytoluene, 3,4-dihydroxytoluene, 3,5-dihydroxytoluene and 6,7-dihydroxy-2-methylnaphthalene), and an aromatic compound having plural hydroxyl groups and methyl groups (e.g., 4,6-dihydroxy-m-xylene and 2,6-dihydroxy-p-xylene).

Aromatic compounds may be substituted with various substituents, for example, a halogen atom (e.g., fluorine, chlorine, bromine and iodine atom), an alkyl group other than methyl group (e.g., ethyl, propyl, butyl, pentyl, hexyl group and other straight chain $C_{2-6}$ alkyl groups), an alkoxy groups (e.g., methoxy, ethoxy, propoxy, butoxy, and other $C_{1-6}$ alkoxy groups), a carboxyl group, an alkoxycarbonyl group (e.g., methoxycarbonyl, ethoxycarbonyl, propoxycarbonyl, butoxycarbonyl, and other $C_{1-6}$ alkoxycarbonyl groups), an amino group, a substituted amino group, a cyano group, and a nitro group. Aromatic compounds having these substituents include, for example, a halogen-containing aromatic compound (e.g., 2-chloro-4-hydroxytoluene and other a chlorine-containing hydroxytoluenes), an aromatic compound containing a $C_{2-6}$ alkyl group (e.g., 2-ethyl-4-hydroxytoluene), an aromatic compound containing an amino group (e.g., 2-amino-4-hydroxytoluene).

A feature of the present invention resides in the oxidation of the methyl group on an aromatic compound with oxygen after a protection of a phenolic hydroxyl group of the aromatic compound by a protecting group, not in the subjecting an aromatic compound to an oxidation reaction directly.

A protecting group includes, for example, t-butyl group, a cycloalkyl group (e.g., cyclohexyl group), an aryl group (e.g., 2,4-dinitrophenyl group), an aralkyl group (e.g., benzyl group, 2,6-dichlorobenzyl group, 3-bromobenzyl group, 2-nitrobenzyl group, 4-dimethylcarbamoylbenzyl group, and triphenylmethyl group), a tetrahydropyranyl group, an acyl group, an alkoxycarbonyl group (e.g., t-butoxycarbonyl group), an aralkyloxycarbonyl group (e.g., benzyloxycabonyl group, 2-bromobenzyloxycarbonyl group), a dialkylphosphinothioyl group (e.g., dimethylphosphinothioyl group) and a diarylphosphinothioyl group (e.g., diphenylphosphinothioyl group). A preferred protecting group includes an acyl group and the like.

The acyl group includes, for example, acetyl, propionyl, butyryl, isobutyryl, valeryl, isovaleryl, pivaloyl, and other $C_{2-6}$ aliphatic acyl groups, preferably $C_{2-4}$ acyl groups.

The protection of a hydroxyl group by a acyl group may be carried by a conventional method, for example, a reaction of aromatic compounds with an acylating agent. The acylating agent includes, for example, acetic acid, propionic acid, n-butyric acid, isobutyric acid, valeric acid, pivalic acid and other $C_{2-6}$ aliphatic monocarboxylic acid (preferably $C_{2-4}$ carboxylic acid) and derivatives thereof [such as anhydrides (e.g., acetic anhydride and valeric anhydride), and acid halides (e.g., acetyl chloride, propionyl chloride, butylyl chloride and other acid chlorides)]. An acylating agent may be used independently or in combination.

The amount of the acylating agent is selected from a range of not less than about 1 mole for example, about 1 to 100 mole, relative to 1 mole of an aromatic compound per a phenolic hydroxyl group. (The oxidation of an aromatic compound protected by a protecting group)

In the present invention, a protected compound is oxidized with oxygen in the presence of an oxidation catalyst (such as an imide compound). In this oxidation process, the methyl group of aromatic compounds protected by the protecting group may be oxidized with oxygen to produce aromatic hydroxycarboxylic acid derivatives, thus no metal salt (e.g., sodium sulfate or potassium sulfate) is produced.

The imide compound includes the compound shown by the following fomula (1);

(1)

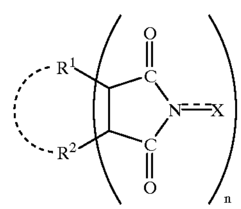

wherein $R^1$ and $R^2$ respectively represent a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond, or an aromatic or non-aromatic ring; X represents an oxygen atom or a hydroxyl group; and n denotes an integer of 1 to 3.

In the compound shown by the formula (1), the halogen atom, as the substituents $R^1$ and $R^2$, includes iodine, bromine, chlorine and fluorine. The alkyl group includes, for example, methyl, ethyl, propyl, isopropyl, butyl, isobutyl, s-butyl, t-butyl, pentyl, hexyl or other $C_{1-10}$ alkyl groups. An illustrative preferred alkyl group includes $C_{1-6}$ alkyl groups, in particular $C_{1-4}$ alkyl groups. As the aryl group, there may be mentioned, for instance, a phenyl group and a naphthyl group. Examples of the cycloalkyl group include cyclopentyl, cyclohexyl, and cyclooctyl group.

The alkoxy group includes, for example, methoxy, -ethoxy, propoxy, isopropoxy, butoxy, isobutoxy, t-butoxy, pentyloxy, hexyloxy, and other $C_{1-10}$ alkoxy groups. Among them, $C_{1-6}$alkoxy groups, in particular $C_{1-4}$ alkoxy groups are preferable. Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other $C_{1-10}$ alkoxycarbonyl groups. Among them, $C_{1-6}$ alkoxy-carbonyl groups, in particular $C_{1-4}$ alkoxy-carbonyl group are preferble. The acyl group includes, for instance, formyl, acetyl, propionyl, butyryl, isobutyryl, valeryl, isovaleryl, pivaloyl, and other $C_{1-6}$ acyl groups.

The substituents $R^1$ and $R^2$ may be either the same or different from each other. In the formula (1), $R^1$ and $R^2$ may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, and it may practically be a hydrocarbon ring. As such a ring, there may be mentioned, for instance, non-aromatic alicyclic rings (e.g., a cycloalkane ring which may have a substituent such as cyclohexane ring, optionally substituted cycloalkene ring such as cyclohexene ring), non-aromatic bridged (cross-linked) rings (e.g., 5-norbornene ring and other optionally substituted bridged hydrocarbon rings), optionally substituted aromatic rings such as a benzene ring or, naphthalene ring. The ring may practically comprise an aromatic ring.

A preferred imide compound includes compounds shown by the following formula (1a) to (1f), (1a)

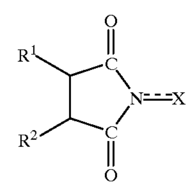

(1b)

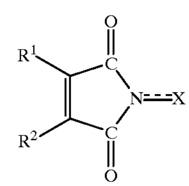

-continued (1c)

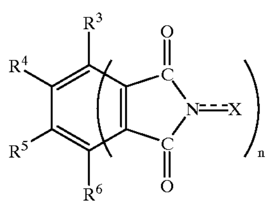

(1d)

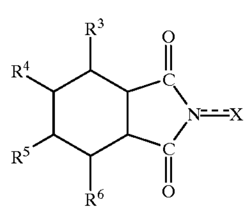

(1e)

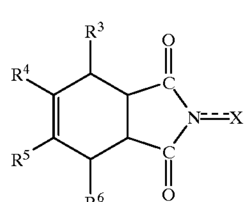

(1f)

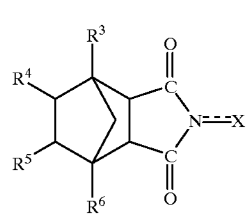

wherein $R^3$, $R^4$, $R^5$ and $R^6$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$ and n have the same meanings as defined above.

In the substituents $R^3$, $R^4$, $R^5$ and $R^6$, the alkyl group, alkoxy group, the alkoxycarbonyl group, the acyl group and the halogen atom include the substituents or atoms exemplified for $R^1$ and $R^2$ The substituents $R^3$, $R^4$, $R^5$ and $R^6$ may practically be hydrogen atoms, alkyl groups having about 1 to 4 carbon atoms, carboxyl groups, nitro groups or halogen atoms, respectively.

The symbol X in the formula (1) denotes an oxygen atom or a hydroxyl group, and n usually denotes about 1 to 3, preferably 1 or 2. The compound shown by the formula (1) may be used singly or in combination in the oxidation reaction.

Examples of a preferred imide compound include an imide compound derived from an aliphatic polycarboxylic anhydride (such as N-hydroxysuccinimide, N-hydroxymaleimide), an imide compound derived from an alicyclic polycarboxylic anhydride or an aromatic polycarboxylic anhydride (such as N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide). These imide compounds have a high oxidizing property. A particularly preferred imide compound includes an N-hydroxyimide compound derived from an alicyclic polycarboxylic anhydride, in particular from an aromatic polycarboxylic anhydride, such as N-hydroxyphthalimide.

The imide compound may be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

An oxidation catalyst may be comprise an imide compound of the following formula (1) and a co-catalyst. The co-catalyst (co-oxidizing agent) includes or comprises metal compounds such as a compound comprising or containing a transition metal compound, or compounds containing a Group 13 element (e.g., boron B, aluminium Al) of the Periodic Table of Elements. These co-catalysts may be employed independently or in combination.

As the elements of the transition metal, there may be mentioned, for instance, Group 3 elements of the Periodic Table of Elements (e.g., scandium Sc, yttrium Y, and lanthanum La, cerium Ce, samarium Sm and other lanthanoid elements, actinium Ac and other actinoid elements), Group 4 elements of the Periodic Table of Elements (e.g., titanium Ti, zirconium Zr, hafnium Hf), Group 5 elements (e.g., vanadium V, niobium Nb, tantalum Ta), Group 6 elements (e.g., chromium Cr, molybdenum Mo, tungsten W), Group 7 elements (e.g., manganese Mn, technetium Tc, rhenium Re), Group 8 elements (e.g., iron Fe, ruthenium Ru, osmium Os), Group 9 elements (e.g., cobalt Co, rhodium Rh, iridium Ir), Group 10 elements (e.g., nickel Ni, palladium Pd, platinum Pt), Group 11 elements (e.g., copper Cu, silver Ag, gold Au) of the Periodic Table of Elements.

A preferred element constituting the co-catalyst includes elements of the transition metals (e.g., Ce and other lanthanoid elements, actinoid elements and other Group 3 elements of the Periodic Table of Elements, Ti, Zr and other Group 4 elements, V, Nb and other Group 5 elements, Cr, Mo, W and other Group 6 elements, Mn, Tc, Re and other Group 7 elements, Fe, Ru and other Group 8 elements, Co, Rh and other Group 9 elements, Ni and other Group 10 elements, and Cu and other Group 11 elements of the Periodic Table of Elements) and B and other Group 13 elements of the Periodic Table of Elements. The oxidation number of the metal elements constituting the co-catalyst is not particularly limited, and may be, for example 0, +2, +3, +4, +5 and +6 according to the variety of elements. The divalent transition metal compounds (such as a divalent cobalt compound, a divalent manganese compound) may be practically used as the co-catalyst.

The species of the co-catalyst may be a simple substance or hydroxide of a metal. The co-catalyst may practically be an oxide of a metal comprising the element, a double oxide comprising the element or an oxygen acid salt comprising the element, an organic acid salt, an inorganic acid salt, a halide, a coordinate compound (a complex) comprising the metal element, or a heteropolyacid or its salt. As the boron compound, there may be mentioned, for example, a boron hydride (e.g., borane, diborane, tetraborane), a boric acid (e.g., orthoboric acid, metaboric acid), a borate (e.g., manganese borate), $B_2O_3$ and other boron oxides, nitrogen-containing boron compounds such as borazne and borazene, halides such as $BF_3$ and $BCl_3$, and esters of boric acid (e.g., methyl borate, phenyl borate).

The hydroxide includes $Mn(OH)_2$, $MnO(OH)$ or a corresponding metal hydroxide (e.g., a titanium hydroxide such as $Ti(OH)_3$, and vanadium hydroxide such as $V(OH)_2$). The metal oxide includes, for example, titanium oxide (such as $TiO_2$), zirconium oxide (e.g., $ZrO_2$), vanadium oxide (e.g., VO, $V_2O_3$, $VO_2$, $V_2O_5$), chromium oxide (e.g., CrO), molybdenum oxide (e.g., $MoO_2$, $Mo_2O_5$, $MoO_3$, $H_2MoO_4$), manganese oxide (e.g., $Mn_2O_3$, $MnO_2$), iron oxide, cobalt oxide (e.g., $CoO_2$), rhodium oxide, copper oxide and so forth. As examples of the double oxide or oxygen acid salt, there may be mentioned $MnAl_2O_4$, $MnTiO_3$, $LaMnO_3$, $K_2Mn_2O_5$, $CaO.xMnO_2$(x=0.5, 1, 2, 3, 5), manganate (e.g., $Na_3MnO_4$ and other manganates (V), $K_2MnO_4$ and other manganates (VI), $KMnO_4$ and other permanganates), titanate (such as $K_2TiO_3$, $K_2Ti_2O_4$), zirconium salt (such as $K_2ZrO_3$), vanadate (such as $K_3VO_4$, $K_4V_2O_7$, $KVO_3$), chromate (such as $K_2CrO_4$) and so forth.

As the organic acid salts, there may be exemplified as acetates (e.g., titanium acetate, zirconium acetate, manganese acetate, iron acetate, cobalt acetate, copper acetate), propionates (e.g., manganese propionate, cobalt propionate), naphthenates (e.g., manganese naphthenate, cobalt naphthenate), stearates (e.g., manganese stearate, cobalt stearate, copper stearate), thiocyanates (e.g., manganese thiocyanate), and corresponding salts of Ce, Ni and Pd. The inorganic acid salt includes, for instance, nitrates (e.g., titanium nitarate, zirconium nitrate, chromium nitarate, manganese nitrate, iron nitrate, cobalt nitrate, copper nitrate and sulfates, phosphates and carbonates each corresponding to these nitrates (e.g., vanadium sulfate, manganese sulfate, iron sulfate, cobalt sulfate, copper sulfate). As the halides, there may be mentioned, for instance, chlorides (such as $TiCl_2$and other titanium chloride; $ZrCl_2$ and other zirconium chloride; $VCl_2$, $VCl_3$, $VCl_4$, $VOCl_2$, $VOCl_3$ and other vanadium chloride; $CrCl_2$ and other chromium chloride; $MoCl_3$ and other molybdenum chloride; $MnCl_2$ and other manganese chloride; $FeCl_2$ and other iron chloride; $CoCl_2$ and other cobalt chloride; rhodium chloride; nickel chloride; palladium chloride; platinum chloride; CuCl, $CuCl_2$ and other copper chloride) and other, or fluorides or bromides (e.g., CuF, $CuF_2$, CuBr, $CuBr_2$ and other copper fluoride or bromide) each corresponding to these chlorides and other halides, $M^1{}_2TiCl_5$, $M^1{}_3TiCl_6$, $M^1{}_2TiCl_6$, $M^1MnCl_3$, $M^1{}_2MnCl_4$, $M^1{}_2MnCl_5$, $M^1{}_2MnCl_6$, wherein $M^1$ represents a monovalent metal, and other complexed halides.

The ligand constituting the complex includes, for example, OH (hydroxy), methoxy, ethoxy, propoxy, butoxy and other alkoxy groups, acetyl, propionyl and other acyl groups, methoxycarbonyl (acetato), ethoxycarbonyl and other alkoxycarbonyl groups, acetylacetonato, cyclopentadienyl group, chlorine, bromine and other halogen atoms, CO, CN, oxygen atom, $H_2O$ (aquo), phosphine (e.g., triphenylphosphine and other triarylphosphine) and other phosphorus compounds, $NH_3$ (ammine), NO, $NO_2$(nitro), $NO_3$ (nitrato), ethylenediamine, di-ethylenetriamine, pyridine, phenanthroline and other nitrogen-containing compounds. In the complexes or complex salts, the same or different ligands may be coordinated singly or in combination. The preferable ligand includes, for example, OH, an alkoxy group, an acyl group, an alkoxycarbonyl group, acetylacetonato, a halogen atom, CO, CN, $H_2O$ (aquo), triphenylphosphine or other phosphorus compounds, or a nitrogen-containing compoundinclusive of $NH_3$, $NO_2$ and $NO_3$.

A preferable complex includes complexes containing a preferable transition metal above mentioned. The transition metal element and the ligand may optionally be employed in combination to form a complex. The complex may include, for instance, acetylacetone complex salt (e.g., acetylacetonatocerium, acetylacetonatotitanium, oxide acetylacetonatotitanium, acetylacetonatozirconium, acetylacetonatovanadium, acetylacetonatovanadium oxide, acetylacetonatochromium, acetylacetonatomolybdenum, acetylacetonatomanganese, acetylacetonatoiron, acetylacetonatocobalt, acetylacetonatoruthenium, acetylacetonatocopper), and carbonyl complex compounds.

The polyacid forming heteropolyacid is practically at least one member selected from Group 5 elements or Group 6 elements of the Periodic Table of Elements, such as V (vanadic acid), Mo (molybdic acid) and W (tungstic acid), typically speaking. There is no particular limit as to the central atom, and it may be any of, for instance, Be, B, Al, Si, Ge, Sn, Ti, Zr, Th, N, P, As, Sb, V, Nb, Ta, Cr, Mo, W, S, Se, Te, Mn, I, Fe, Co, Ni, Rh, Os, Ir, Pt, or Cu. As illustrative examples of the heteropolyacid, there may be mentioned, for example, cobaltmolybdic acid, cobalttungstic acid, molybdenumtungstic acid, vanadiummolybdic acid, vanadiumtungstic acid, silicomolybdic acid, silicotungstoic acid, phosphomolybdic acid, phosphotungstic acid, phosphovanadomolybdic acid, and phosphovanadotungstic acid.

Catalytic system comprising an imide compound shown by formula (1) or the imide compound and the above co-catalyst may be whichever of a homogeneous system or a heterogeneous system. The catalytic system may be a solid catalyst comprising a catalytic component supported on a support or carrier, as well. As the support, use can be practically made of active carbon, zeolite, silica, silica-alumina, bentonite, or other porous supports. In the solid catalyst, a supporting amount of the imide compound of the formula (1) may be about 0.1 to 50 parts by weight, preferably about 0.5 to 30 parts by weight and more preferably about 1 to 20 parts by weight relative to 100 parts by weight of the support. A ratio of the cocatalyst supported on the support is about 0.1 to 30 parts by weight, preferably about 0.5 to 25 parts by weight, and more preferably about 1 to 20 parts by weight, relative to 100 parts by weight of the support.

The amount of the imide compound shown by the formula (1) may be selected from a wide range and be, for example about 0.001 mole (0.1 mole %) to 1 mole(100 mole %), preferably about 0.001 mole (0.1 mole %) to 0.5 mole (50 mole %), more preferably about 0.01 to 0.30 mole and practically about 0.01 to 0.25 mole, relative to 1 mole of aromatic compounds protected by a protecting group, typically speaking.

An amount of the co-catalyst (a co-oxidizing agent) may be, for example, about 0.0001 mole (0.1 mole %) to 0.7 mole (70 mole %), preferably about 0.0001 to 0.5 mole, and more preferably about 0.001 to 0.3 mole, practically about 0.0005 to 0.1 mole (for example 0.005 to 0.1 mole), relative to 1 mole of aromatic compounds protected by a protecting group, typically speaking.

The proportion of the co-catalyst relative to the imide compound of the formula (1) can be selected from a range not interfering with the reaction velocity or rate and selectivity, and is for example, about 0.001 mole to 10 mole, preferably about 0.005 to 5 mole, more preferably about 0.01 to 3 mole, and practically about 0.01 to 5 mole, relative to 1 mole of the imide compound, typically speaking.

When the heteropolyacid or its salt may be used as a co-catalyst, the amount is about 0.1 to 25 parts by weight, preferably 0.5 to 10 parts by weight, and more preferably 1 to 5 parts by weight relative to 100 parts by weight of aromatic compounds protected by a protecting group.

In the presence of the oxidation catalyst, aromatic compounds protected by a protecting group is contacted with oxygen to selectively oxidize a methyl group of the aromatic compounds and to quantitatively produce aromatic hydroxycarboxylic acid derivatives (which are aromatic hydroxycarboxylic acids protected by a protecting group) with a high conversion and selectivity. For example, acyloxytoluene or acyloxymethylnaphtalene is subjected to the oxidation reaction with oxygen to produce acyloxybenzoic acid or acyloxynaphthoic acid.

The oxygen used in the oxidation reaction may be active oxygen, but molecular oxygen is practically employed for advantages. Such molecular oxygen is not specifically limited, and use may be made of whichever of pure oxygen, or oxygen diluted with an inert gas such as nitrogen, helium, argon or carbon dioxide gas. Air is preferably employed from the viewpoint of not only handling property and safety, but also economical property.

The amount of oxygen is, for example, 0.5 mole or more (e.g., 1 mole or more), preferably about 1 to 100 moles, and more preferably about 2 to 50 moles relative to 1 mole of aromatic compounds protected by a protecting group per a methyl group.

An oxidation reaction is usually conducted in an inert solvent. As the organic solvents, there may be mentioned, for example, protonic acids (such as organic acids (e.g., acetic acid, propionic acid and other carboxylic acids, methanesulfonic acid, ethanesulfonic acid and other alkylsulfonic acids, and benzensulfonic acid and other arylsulfonic acids), inorganic acids (e.g., hydrochloric acid, sulfuric acid, nitric acid and phosphoric acid)), nitriles (e.g., acetonitrile, propionitrile, benzonitrile), amides (e.g., formamide, dimethylformamide), alcohols (e.g., ethanol, propanol, butanol), aliphatic hydrocarbons (e.g., hexane, octane), aromatic hydrocarbons (e.g., benzene), halogenated hydrocarbons (e.g., chloroform), nitro compounds (e.g., nitromethane, nitrobenzene), esters (e.g., ethylacetate), ethers (e.g., diethyl ether, dioxane, tetrahydrofuran) and mixtures of these solvents. Incidentally, when organic carboxylic acids (e.g., acetic acid, propionic acid) may be used as a solvent, aromatic compounds can be subjected to oxidation reaction without protection of a phenolic hydroxyl group by a protecting group.

The oxidation reaction smoothly proceeds even in comparatively mild or moderate conditions. A reaction temperature can be voluntarily selected according to the variety of the imide compound and the aromatic compounds protected by a protecting group. The reaction temperature may be suitably selected from the range of, for instance, about 0 to 300° C., preferably about 30 to 250° C., more preferably about 50 to 200° C., and practically about 70 to 150° C. (e.g., 70 to 120° C.). The reaction may be carried out at ambient pressure (atmospheric pressure) or under a pressure (under a load). When the reaction is conducted under a pressure, the pressure is, usually, about 1 to 100 atm (e.g., about 1.5 to 80 atm), preferably about 2 to 70 atm, and more preferably about 5 to 50 atm. A reaction time may be liberally chosen within a range of about 30 minutes to 48 hours, preferably about 1 to 36 hours, and more preferably about 2 to 24 hours, according to the reaction temperature and pressure. The reaction may be effected in a conventional manner such as in a batch system, semi-batch system or continuous system, in the presence of molecular oxygen or under flow of molecular oxygen.

(The elimination (removal) of a protecting group)

Aromatic hydroxycarboxylic acids obtained by the oxidation reaction and containing a phenolic hydroxyl group therein protected by a protecting group may be subjected to an elimination reaction to eliminate the protecting group. Elimination of the protecting group of a hydroxyl group may be carried by a conventional method, for example, a reaction of aromatic compounds protected by a protecting group with an acid or a base. Acids includes, for example, inorganic acids (e.g., hydrochloric acid, sulfuric acid, nitric acid, phosphoric acid), organic acids (e.g., methanesulfonic acid, ethanesulfonic acid, benzenesulfonic acid, p-toluenesulfonic acid and other sulfonic acids), and acidic ion-exchange resins (e.g., ion-exchange resins having a sulfo residue, a phospho residue, or a phosphine residue), boron trifluoride and other Lewis acids. A base includes, for example, a compound containing basic nitrogen atom, such as dimethylamine, diethylamine, trimethylamine, trimethylamine, methylenediamine, ethylenediamine, and other aliphatic amines, pyridine, morpholine and other heterocyclic amines.

An aromatic hydroxycarboxylic acid obtained by the oxidation reaction and the phenolic hydroxyl group therein protected by an acyl group may be reacted with an alcohol to eliminate the acyl group. In this reaction, acids or bases mentioned hereinbefore may be used as a catalyst.

The alcohol includes, for example, methanol, ethanol, propanol, isopropanol, n-butanol, isobutanol, sec-butanol, t-butanol, 1-pentanol, 1-hexanol, 1-heptanol, 1-octanol, 2-ethylhexanol and other $C_{1-10}$ saturated aliphatic monoalcohols (preferably $C_{1-6}$ alcohols, and more preferably $C_{1-4}$ lower alcohols). Such alcohol may be employed independently or in combination.

The amount of alcohol is selected from a range, and may be, for example, not less than 1 mole (e.g., about 1 to 100 mole), preferably about 1 to 50 mole (e.g., about 1 to 20 mole), and more preferably about 2 to 10 mole relative to 1 mole of the aromatic acyloxycarboxylic acid per an the acyloxy group. Alcohol is practically used in an excess amount.

The aromatic hydroxycarboxylic acid protected by an acyl group is reacted with alcohol to produce the aromatic hydroxycarboxylic acid or derivative thereof (such as hydroxybenzoate, hydroxynaphtoate and other aromatic hydroxycarboxylates) having a free hydroxyl group. For example, an acyloxybenzoic acid is reacted with methanol to produce methyl hydroxybenzoate. Acyloxybenzoic acid is reacted with $C_{2-4}$ alcohols to produce hydroxybenzoic acid-$C_{2-4}$ alkylesters which are useful as an antibacteria agent, particularly a stock agent of a refreshment beverage. Aromatic hydroxycarboxylates are considerably useful as raw materials of polyesters.

Aromatic hydroxycarboxylic acid derivatives, catalysts (such as an imide compound), solvents and the like may be recovered by a conventional isolation method, such as filtration, condensation, distillation, crystallization, extraction, recrystallization, column chromatography, or in combination thereof. Recovered catalysts or solvents may be recycled.

INDUSTRIAL APPLICABILITY OF THE INVENTION

In the present invention, since a methyl group-containing an aromatic compound wherein a phenolic hydroxyl group thereof is protected by a protecting group are oxidized with oxygen in the presence of an oxidation catalyst comprising an imide compound, aromatic hydroxycarboxylic acid derivatives are efficiently produced. Aromatic hydroxycarboxylic acid derivatives may be produced without producing a metal salt as by-products.

EXAMPLES

The following examples are intended to describe this invention in further detail and should by no means be interpreted as defining the scope of the invention.

Example 1

A mixture of p-cresol (1.08 g (10 mmole)) and acetic acid (25 ml) was stirred for 5 hours at 110° C. to produce p-acetoxytoluene. N-hydroxyphthalimide (0.16 g (1 mmole)) and cobalt(II) acetylacetonate (0.018 g (0.05 mmole)) were added to this reaction mixture, and this mixture was stirred for 6 hours at 100° C. under an oxygen atmosphere. The product in the resultant reaction mixture was analyzed by gas chromatography and, as a result, p-acetoxybenzoic acid (yield 92%) was formed. The conversion of p-cresol was 95%.

The reaction mixture was condensed to remove substances having a lower boiling point such as acetic acid. Followed by adding 3 times mole of methanol relative to p-acetoxybenzoic acid and 5 times equivalents of a cation-exchange resin (DIAIONBK-210; MITSUBISHI chemical Co.) relative to p-acetoxybenzoic acid as an amount of an ion-exchange group to stir for 4 hours at 60° C. As a result, methyl p-acetoxybenzoate (yield 91%) was formed. The conversion of p-acetoxybenzoic acid was 95%.

What is claimed is:

1. A process for producing an aromatic hydroxycarboxylic acid derivative which comprises contacting an aromatic compound with oxygen in the presence of an imide compound as a catalyst, wherein said aromatic compound has a methyl group and a phenolic hydroxyl group protected by a protecting group and said imide compound is shown by the following formula (1)

(1)

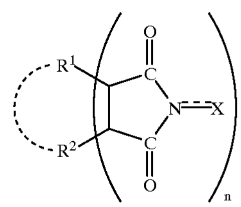

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may bond together to form a double bond or an aromatic and non-aromatic ring; X represents an oxygen atom or a hydroxyl group; and n denotes an integer of 1 to 3.

2. The process for producing an aromatic hydroxycarboxylic acid derivative according to claim 1, wherein said protecting group is an aliphatic acyl group having 2 to 6 carbon atoms.

3. The process for producing an aromatic hydroxycarboxylic acid derivative according to claim 1 or 2, which further comprises subjecting the aromatic hydroxycarboxylic acid, which is obtained by contacting with oxygen and contains a phenolic hydroxyl group protected by the protecting group, to an elimination reaction of a protecting group to produce a free hydroxyl group.

4. The process for producing an aromatic hydroxycarboxylic acid derivatives according to claim 2, which further comprises the step of reacting the aromatic hydroxycarboxylic acid, which is obtained by a contacting with oxygen and contains the phenolic hydroxyl group protected by an acyl group, with an alcohol to produce an aromatic hydroxycarboxylic ester having a free hydroxyl group.

5. A process for producing an hydroxybenzoic acid or an ester thereof which comprises the steps of contacting an acyloxytoluene with oxygen in the presence of an imide compound represented by the following formula (1)

(1)

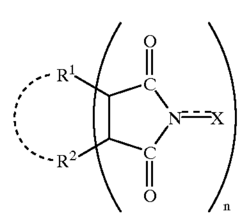

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may bond together to form a double bond or an aromatic and non-aromatic ring; X represents an oxygen atom or a hydroxyl group; and n denotes an integer of 1 to 3;

to produce an acyloxybenzoic acid and reacting the acyloxybenzoic acid with an alcohol.

6. The process for producing an aromatic hydroxycarboxylic acid derivative according to claim 1, wherein $R^1$ and $R^2$, in said imide compound shown by the formula (1), bond together to form an aromatic or a non-aromatic 5 to 12 membered ring.

7. The process for producing an aromatic hydroxycarboxylic acid derivative according to claim 1, wherein $R^1$ and $R^2$, in said imide compound shown by the formula (1), bond together to form a cycloalkane ring which may have a substituent, a cycloalkene ring which may have a substituent, a bridged hydrocarbon ring which may have a substituent and an aromatic ring which may have a substituent.

8. The process for producing an aromatic hydroxycarboxylic acid derivative according to claim 1, wherein said imide compound shown by the formula (1) is a compound shown by the following formulas (1a), (1b), (1c), (1d), (1e) and (1f);

(1a)

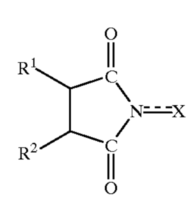

(1b)

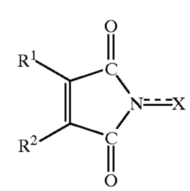

-continued (1c)

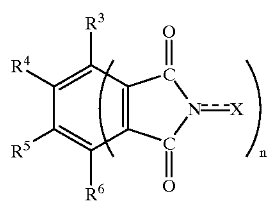

(1d)

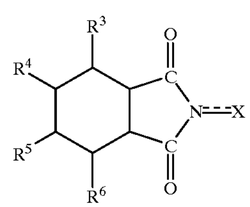

(1e)

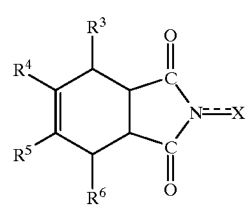

(1f)

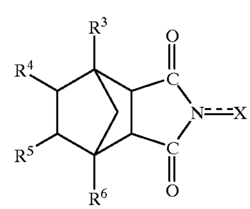

wherein $R^3$, $R^4$, $R^5$ and $R^6$ are the same or different a hydrogen atom, an alkyl group, a hydroxyl group, an alkoxy group, a carboxyl group, an alkoxycarbonyl group, an acyl group, a nitro group, a cyano group, an amino group or a halogen atom; and $R^1$, $R^2$ and n have the same meanings as defined in claim 1.

9. The process for producing an aromatic hydroxycarboxylic acid derivative according to claim 1, wherein said imide compound shown by the formula (1) is at least one compound selected from the group consisting of N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide and N,N'-dihydroxynaphthalenetetracarboximide.

10. The process for producing an aromatic hydroxycarboxylic acid derivative according to claim 1, wherein said catalyst comprises the imide compound shown by the formula (1) and a co-catalyst.

11. The process for producing an aromatic hydroxycarboxylic acid derivative according to claim 10, wherein said co-catalyst is a compound containing at least one element selected from the group consisting of transition metal elements and Group 13 elements of the Periodic Table of Elements.

12. The process for producing an aromatic hydroxycarboxylic acid derivative according to claim 10, wherein said co-catalyst is a compound containing at least one element selected from the group consisting of Group 3 elements, Group 4 elements, Group 5 elements, Group 6 elements, Group 7 elements, Group 8 elements, Group 9 elements, Group 10 elements and Group 11 elements of the Periodic Table of Elements.

* * * * *